United States Patent [19]

Boute et al.

[11] Patent Number: 4,554,921
[45] Date of Patent: Nov. 26, 1985

[54] DUAL CHAMBER PACEMAKER WITH AUTOMATIC HIGH RATE LIMIT MODE DETERMINATION

[75] Inventors: Wim Boute, Doesburg; Frederik H. M. Wittkampf, Brummen; Gerrit W. van Arragon, Dieren, all of Netherlands

[73] Assignee: Vitafin N.V., Curacao, Netherlands Antilles

[21] Appl. No.: 566,059

[22] Filed: Dec. 27, 1983

Related U.S. Application Data

[63] Continuation-in-part of Ser. No. 465,890, Feb. 11, 1983.

[51] Int. Cl.⁴ ............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,059,116 | 10/1977 | Adams | 128/419 PG |
| 4,401,119 | 8/1983 | Herpers | 128/419 PG |
| 4,429,697 | 2/1984 | Nappholz et al. | 128/419 PG |
| 4,452,248 | 6/1984 | Keller, Jr. | 128/419 PG |

FOREIGN PATENT DOCUMENTS

| | | | |
|---|---|---|---|
| 0050038 | 4/1982 | European Pat. Off. | 128/419 PG |
| 81209 | 6/1983 | European Pat. Off. | 128/419 PG |
| WO82/48211 | 11/1982 | PCT Int'l Appl. | 128/419 PG |

*Primary Examiner*—William E. Kamm
*Attorney, Agent, or Firm*—Woodcock Washburn Kurtz Mackiewicz & Norris

[57] ABSTRACT

A programmable dual chamber cardiac pacemaker is provided which provides improved means for responding to sensed high atrial rates. The pacemaker monitors the sensed high atrial rates and determines whether they are physiological or not, and automatically controls the operative atrial refractory period as a function of whether or not the atrial rate is physiological. The pacemaker is permitted to go into a Wenckebach mode of operation only when it is determined that a sensed high atrial rate is physiological, and that under other conditions will automatically go into a block mode of operation.

11 Claims, 14 Drawing Figures

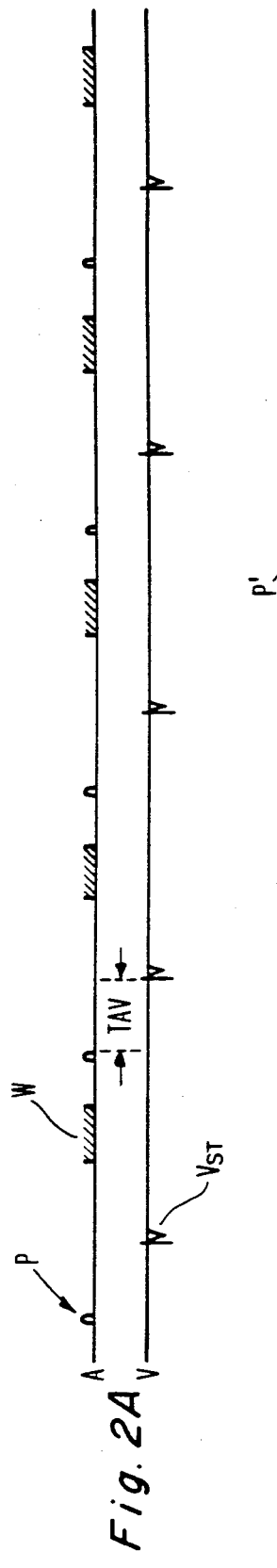
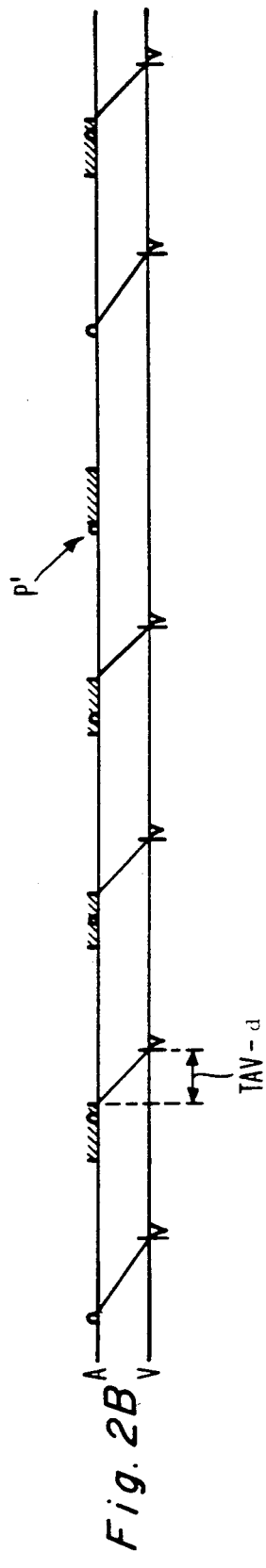
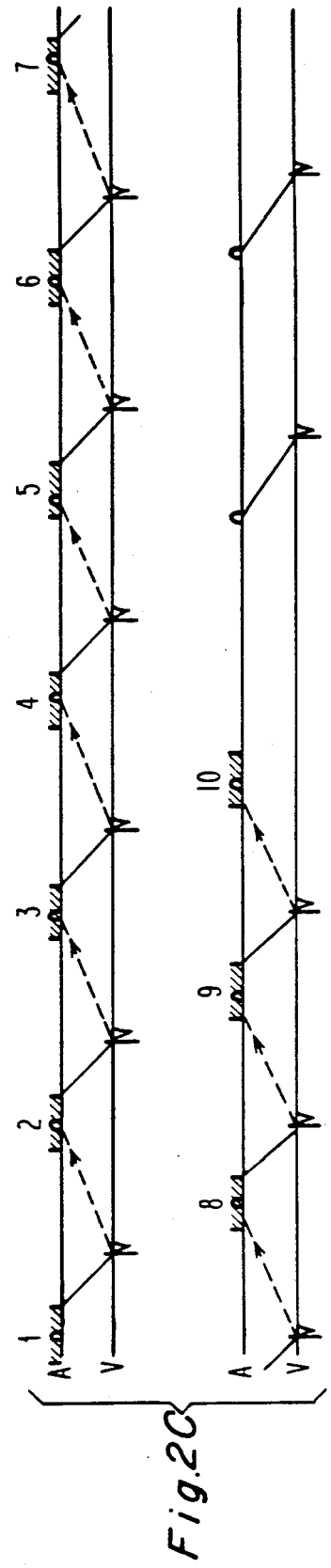

DUAL CHAMBER PACEMAKER WITH AUTOMATIC HIGH RATE LIMIT MODE DETERMINATION

CROSS-REFERENCE TO RELATED APPLICATION

This application is a continuation-in-part of co-pending U.S. application Ser. No. 465,890, filed Feb. 11, 1983, assigned to the same assignee.

BACKGROUND OF THE INVENTION

This invention relates to cardiac pacemakers and, more particularly, to dual chamber cardiac pacemakers adapted to be operated in a plurality of operating modes, including a mode which incorporates P wave synchronous operation, e.g. VDD, DDD. The invention is directed primarily to automatic adapting to sensed high atrial rates.

The advantages of cardiac pacing in different modes, selected to different patient conditions, is now well recognized in the art. Early pacer systems were solely ventricular, which was sufficient for management of patients with complete heart block and Stokes-Adams attacks. However, ventricular pacemakers, even when demand pacemakers, are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (A-V) interval. Such a pacemaker allows the atrium to control the heart's response rate, the ventricle being paced at the atrial rate up to a predetermined upper rate limit. Such synchronous pacers have incorporated means for pacing the ventricle at a 1:2 rate relative to the atrium, or even higher ratio, when the sensed atrial rate exceeds the predetermined maximum rate.

Another form of A-V, or dual chamber pacer that has been utilized is the sequential pacemaker (DVI), with only ventricular sensing and pacing in both the atrium and the ventricle, with an appropriate A-V delay which is timed by the pacemaker. Other pacing modes have been developed, and are classified in accordance with the commonly adopted ICHD code system. In this classification system, the first letter represents the chamber(s) paced (A for atrium; V for ventricle; D for dual), the second letter represents the chamber(s) sensed, and the third letter represents the sensing function, i.e. inhibited (I), trigger (T), dual (D). Known pacing modes include AOO, AAI, AAT, VAT, VDD, VOO, VVI, VVT, VDD, DVI, DOO and DDD. Other codes are used to represent programmability and means for dealing with tachycardia.

With the advent of programmability of pacemakers, as well as improved lead systems for transmitting electrical signals to and from the atrium as well as the ventricle, dual chamber modes of operation are becoming more common and are expected to receive increased use. The advantages of the DDD, or universal pacer are being more widely considered. In plural operating mode systems, which include P wave (or atrial) synchronous operation, it has been known that pacemaker induced, or mediated tachycardia can be a problem. The problem is caused by the retrograde transmission from the ventricle to the atrium of an electrical signal due to a delivered ventricular stimulus pulse, thereby inducing a retrograde P wave. If the pacemaker is permitted to trigger V stimuli on these retrograde P waves then a dangerous pacemaker mediated, i.e. supported, tachycardia results, which should somehow be controlled.

Another problem that exists in operating in any mode which involves P wave synchronous operation originates from attempts to maintain ventricular pacing at a rate no greater than a predetermined maximum rate, even when the natural atrial signal is above such rate. One prior art means of achieving this is to effectively extend the A-V interval for a number of pacer cycles, so that the pacing rate does not exceed the predetermined maximum during those cycles, and then occasionally skip a ventricular pulse and come back into normal synchronous operation. However, this means of operation carries the risk of excessively long actual A-V times, which can have a detrimental effect, including establishing conditions favorable to pacemaker mediated tachycardia. There is thus a need for automatically adjusting pacer operation, for example by adjusting the effective atrial refractory period, in the presence of sensed high atrial rates.

SUMMARY OF THE INVENTION

It is an object of this invention to provide an improved dual chamber pacemaker, having means for detecting and breaking up pacemaker induced tachycardia.

It is another object of this invention to provide a pacemaker system having an improved method of monitoring the occurrence of retrograde P waves, and a method and means for altering pacemaker performance so as to discontinue or alter pacing in such a way as to avoid and break up pacemaker supported tachycardia characterized by retrograde P waves.

It is another object of this invention to provide a programmable cardiac pacemaker, having one or more modes which include A-V synchronous operation, having means for improved synchronous pacing under circumstances where the natural atrial rate exceeds a predetermined pacer maximum rate, while maintaining a substantially stable mean value of A-V delay for delivered ventricular stimulus pulses.

It is a further object of this invention to provide a pacemaker adaptable for dual chamber operation, having improved means and an improved method of high rate A-V operation, including determining when a sensed high atrial rate is physiological or not and adjusting the operative atrial refractory rate in accordance with such determination.

It is another object of this invention to provide a pacing system having automatic means for responding to sensed high atrial rates by adjusting the operative atrial refractory period as a function of whether such high rate appears to be physiological.

It is another object of this invention to provide a pacemaker having improved means for altering the pacemaker operation at rates above a predetermined high frequency limit, in order to achieve improved high rate synchronous operation, and for operating at a reduced operative atrial refractory period only when the patient history indicates that the high rate is physiological.

It is another object of this invention to provide a cardiac pacemaker with means for controlling synchronous operation when the natural atrial rate of the patient is detected to be above a predetermined high rate limit, having improved means for processing sensed atrial rate changes to control the pacemaker to automatically go into a selected high rate mode of operation.

In accordance with the above objects, there is provided a programmable dual chamber cardiac pacemaker, having means for synchronous pacing, having the improvement of means for monitoring the V-A stability of paced operation, and for determining as a function of said monitoring the existence of pacemaker mediated tachycardia due to retrograde P waves. Means are provided for breaking up the pacemaker induced tachycardia, such as by skipping a ventricular stimulus which would normally be delivered in synchronous response to a sensed P signal. The pacer also provides improved means for responding to sensed high atrial rates which exceed a predetermined maximum limit, including means for automatically switching the operative atrial refractory period as a function of whether or not the atrial rate is physiological.

BRIEF DESCRIPTION OF THE DRAWINGS

FIG. 2A is an A/V timing diagram, illustrating dual chamber operation utilizing a high rate sense window (Wenckebach mode), with a normal heart rate.

FIG. 2B is an A/V timing diagram of a first embodiment of this invention, illustrating dual chamber operation where the natural atrial rate exceeds a predetermined maximum limit established by the normal atrial refractory period, with provision for maintaining the mean ventricular stimulus rate below the predetermined high rate limit and for maintaining the actual P-R (A-V) interval at an average value equal to the normal pacer A-V delay.

FIG. 2C is an A/V timing diagram of the first embodiment, illustrating operation of the pacer during pacemaker supported tachycardia, as well as breakup of the tachycardia.

DESCRIPTION OF THE PREFERRED EMBODIMENTS

In the following description of dual chamber pacemaker operation, the letters P and A are used interchangeably. P is normally used to represent the P wave portion of the ECG signal, whereas A is used more broadly to describe an atrial signal, either a sensed atrial beat (P signal) or delivered atrial stimulus pulse. The term "synchronous" operation refers to P wave synchronous operation, wherein a generated ventricular stimulus pulse is timed to be delivered to the ventricle following a given delay ($T_{AV}$) after the atrial signal. Such synchronous operation takes place in, for example, the VDD and DDD pacemaker types of operation.

Figure 1:
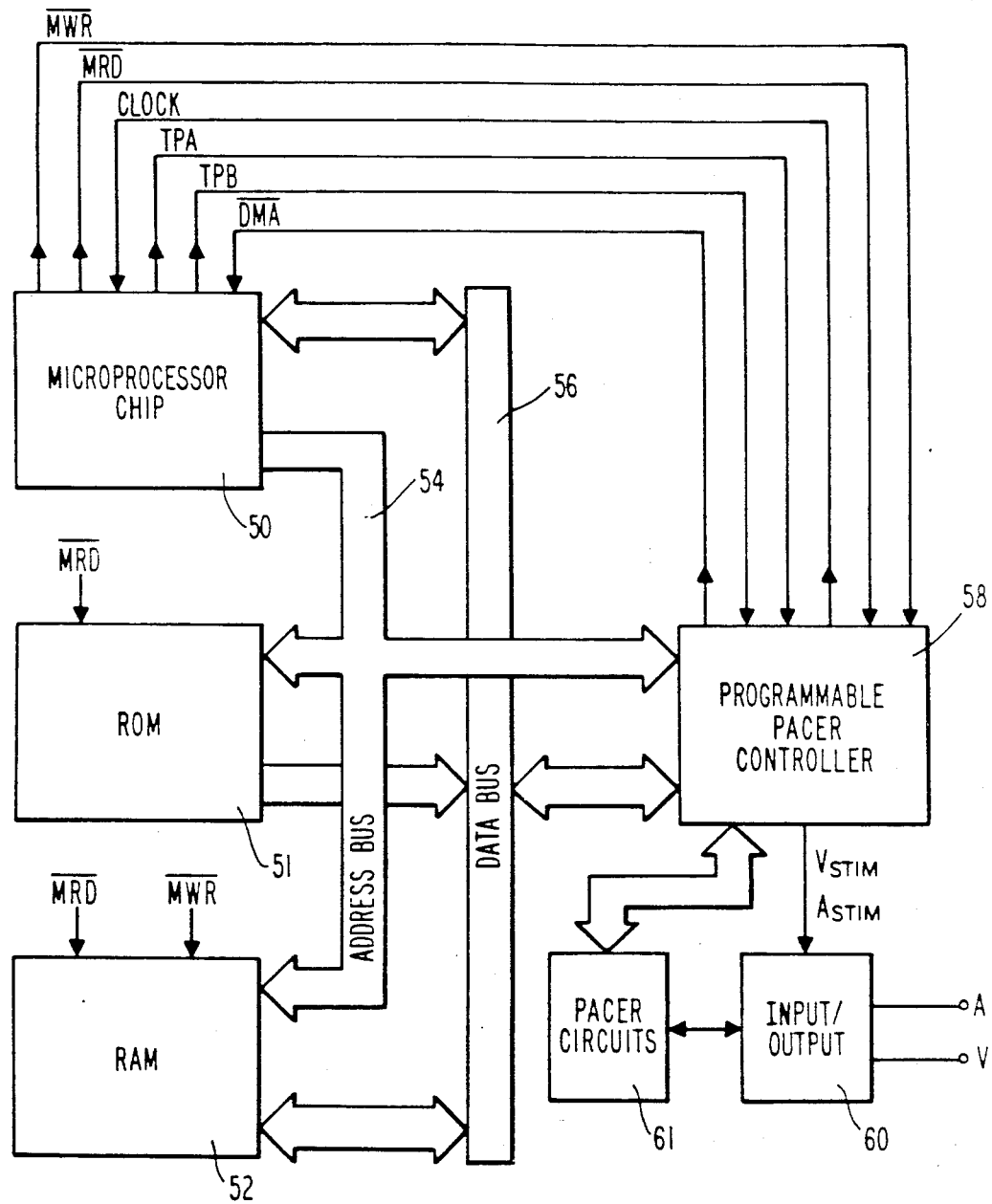
FIG. 1 is an overall block diagram of the pacemaker system of this invention, showing the primary pacemaker system components as used in practicing the method of this invention.

Referring now to FIG. 1, there is shown a block diagram of the primary components of the apparatus of this invention. Shown in block 50 is a microprocessor chip, and as used hereinafter the term microprocessor or microprocessor element means a commercially available microprocessor, whether of one or more chips. A preferred microprocessor for use in the application of this invention as part of a programmable cardiac pacer is the CDP 1802 microprocessor made by RCA. The CDP 1802, hereinafter the 1802, is fabricated on a single chip utilizing a silicon gate CMOS structure. Because of its CMOS structure it offers the design advantages of wide operating temperature range, relatively high speed, high noise immunity and in particular low power consumption. It is to be understood that particularly for an implantable pacer application, where the lifetime of a battery source is important, a low power CMOS microprocessor is particularly advantageous. It is to be understood that other microprocessors are suitable for use in this invention.

Descriptions and specifications of the CDP 1802 are freely available and in the technical literature, and accordingly a full description of the microprocessor is not necessary in this specification. However, some further comments are useful for clarifying the description of this invention. The CDP 1802 has a 40 pin circuit. A standard bidirectional parallel data bus 56 utilizes 8 pins, BUS 0-BUS 7. All parallel data communications between the CPU and external logic, memory or I/O occur via this data bus. There is an 8 bit address bus, represented by the numeral 54. All addresses must be multiplexed; the high order address byte is first outputted, followed by the low order address byte. It is to be noted that compatible memory is used with the CDP 1802 which includes address decode logic. There are 7 status flag pins, including Data Flag and Interrupt Enable Flag, 4 I/O flags and a Q Status Flag which can be set or reset directly by appropriate instructions. There are 4 timing signals, namely CLOCK, XTAL, TPA and TPB. CLOCK is the principle timing signal, inputted from a clock found in programmable pacer controller 58 and controlled by logic within that controller. The frequency of the clock can be up to 6.4 MHz, but for this application may be about 40 KHz. When using the on-chip clock logic of the microprocessor, an external crystal must be connected with a parallel resistor to the XTAL and clock pins. TPA and TPB are timing pulses output by the microprocessor each machine cycle, to control external logic. The remaining pins are control pins, only three of which are illustrated here. MWR and MRD control the memory operation. MWR is output as a low pulse after the second (low order) byte of an address has been paced on the address bus. MWR indicates a memory access operation. MRD indicates the direction of data access; if MRD is low, then the microprocessor is reading data from memory or I/O devices, while if MRD is high, then the microprocessor is writing to memory or I/O devices. The remaining control line shown connected to a pin of the microprocessor is DMA, for DMA operation.

Still referring to FIG. 1, the address bus 54 is shown interconnected with ROM memory 51, RAM memory 52, and the programmable pacer controller circuit 58.

The ROM is suitably an RCA model CPD 1833 chip or equivalent, while the RAM is suitably an RCA model CDP 1822 chip or equivalent. The data bus 56 interconnects the microprocessor chip 50 with ROM 51, RAM 52 and pacer controller 58. Although only one ROM and one RAM block are shown, it is to be understood that there is no limitation on the amount of memory, subject only to design considerations. As further shown in FIG. 1, timing signals represented as $V_{stim}$ and $A_{stim}$ are connected from controller 58 to a conventional output stage which is part of input/output block 60, for developing an output signal to be delivered to a patient's heart. Sensed P and R waves are inputted from block 60 to circuits 61. It is to be understood that for a pacer application other conventional circuitry is incorporated, including timing logic for determining the rate and circumstances for delivering output pulses; A and V sense paths for processing inputted heart signals; receiving means for receiving external program signals and modifying operating parameters in accordance with such external signal; etc. All these functions are conventional and well described in the patent literature, and are represented by block 61 which is shown communicating with controller 58 and input/output block 60.

Figure 2D:
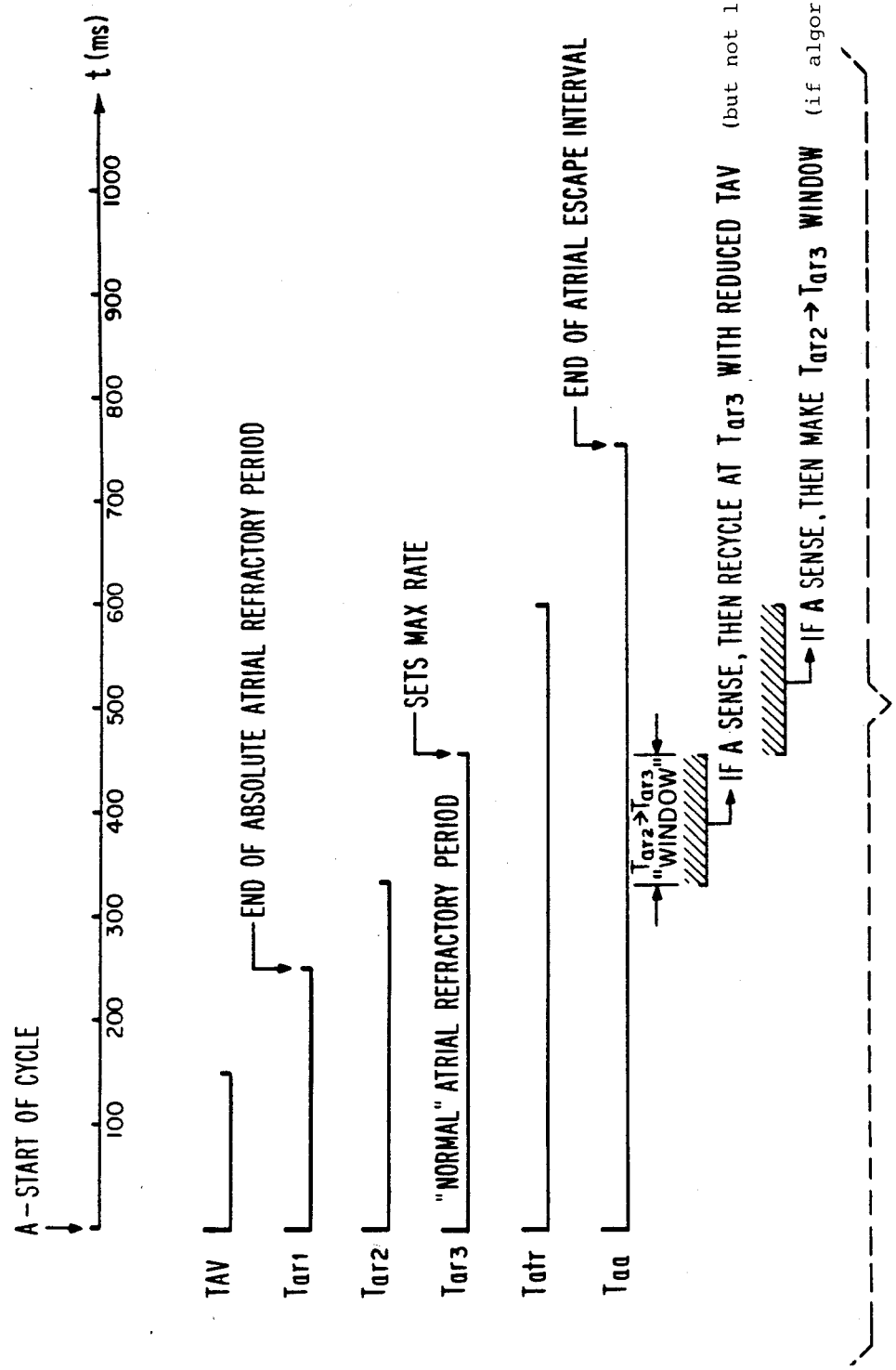
FIG. 2D is a graph illustrating time intervals timed out during each pacer cycle of the pacemaker of the first embodiment of this invention.

Referring now to FIG. 2A, there are shown parallel graphs of atrial (A) and ventricular (V) operation, under normal conditions. As explained below, the basic timing for the pacer system of this invention is from atrial signal to atrial signal, such that the pacer timing normally recycles upon a delivered atrial stimulus or a sensed P signal. The atrial graph of FIG. 2A presents normal operation, with a physiological atrial rate below the predetermined pacer rate limit. The P signals are shown as occurring substantially periodically, i.e., at a constant rate. A window W, sometimes referred to as the "Wenckebach" window, is illustrated, representing a range of time during which the pacer may be enabled to sense P wave signals, and upon so sensing may respond in a specific manner. The window W is also illustrated in the graph of time intervals shown in FIG. 2D. On the ventricular (V) graph, the ventricular stimulus signals $V_{st}$ are shown, being positioned at a time T following each P wave signal.

Referring to FIG. 2B, there is illustrated the pacer mode of operation when a high physiological atrial rate is present, and specifically when the atrial rate exceeds the arbitrarily predetermined maximum rate limit. In this illustration, the window W is enabled. As illustrated, the first V stimulus occurs following a normal $T_{AV}$ interval after the sensed P signal. However, the next P signal is illustrated as falling in the window W. In the pacer mode of operation as described herein, the pacer timing is recycled at the end of the window W, following which a reduced AV interval, for example in the amount $T_{AV}$- d, is timed out. The increment d may be W/2, or it may be determined as described in connection with the preferred embodiment of FIGS. 4 and 5. It is seen that, for such a physiologically natural high rate, the P signal proceeds "backwards" through the window until it appears prior to the start of the window. The first P signal to occur prior to the window, designated P', is ignored for purposes of synchronous operation, i.e., no ventricular stimulus is delivered thereafter. The absence of this ventricular stimulus reduces the mean, or average ventricular stimulus rate to a value below the predetermined maximum limit. Further, by reducing the delay following the end of the window to the next delivered ventricular stimulus, the average delay between the natural P wave and the delivered ventricular stimulus VST is maintained at about $T_{AV}$, which is the predetermined optimum value.

Referring now to FIG. 2C, there are shown curves illustrating the monitoring of pacemaker supported tachycardia, and the pacemaker response to breakup such tachycardia, in accordance with this invention. As described more fully below in connection with the flow diagram of FIG. 3A, whenever an atrial P signal falls within the Wenckebach window W, a counter is incremented, providing an indication of the successive number of P signals sensed to have fallen within the window. In the case of retrograde P waves resulting from the pacemaker ventricular stimulus pulses, each retrograde P occurs at substantially the same time interval following the delivered VST. Since time zero for the pacer cycle starts at the end of the window W, and not at the time of the sensed P signal, and since the retrograde conduction time from ventricle to atrium is substantially constant, each sensed retrograde P signal will fall in the window, which is positioned to "see" such P wave. The timing of the window is such that retrograde P waves will fall within it, and be recognized as such. This is contrasted with the condition of physiological high rate atrial activity, as seen in FIG. 2B, where the sensed P signal shifts through the window after a number of cycles. As illustrated in FIG. 2C, P signals occurring within the window are counted up to an arbitrary number, e.g. 10, following which one V stimulus is skipped. Alternately, as illustrated in the preferred embodiment of FIGS. 3A and 3B, after the 9th P signal is counted, the window is closed the next cycle. Although a 10th retrograde P occurs during the window time, it is not sensed. It is important to note that the dropping of a single ventricular stimulus pulse is effective in terminating such pacemaker supported, or induced tachycardia, since no retrograde P can occur in the absence of a ventricular stimulus.

FIG. 2D is a series of graphs, illustrating the basic time out intervals which are utilized by a first embodiment of the pacemaker of this invention during each pacer cycle. It is to be understood, of course, that other intervals may be timed out, for other purposes, but only the intervals material to an explanation of the invention are shown. The $T_{AV}$ interval is the normal AV delay, which is timed out after the occurrence of a P signal, i.e. at the beginning of a cycle which is designated at the top line by the letter "A". The time $T_{ar1}$ represents the end of the absolute atrial refractory period. After the time out of $T_{ar1}$, the pacer looks for any P signal which might occur, for the purpose of determining the presence of a PVC. For the purposes of this invention, a PVC, or Premature Ventricular Contraction, is defined as a sensed R signal which is not preceded by an atrial signal. The time $T_{ar2}$ is used to define the front end of the window W, which window is illustrated as terminating at time $T_{ar3}$, which is the end of the normal atrial refractory period. $T_{ar3}$ sets the maximum atrial rate corresponding to which ventricular stimulus pulses are generated on a one-to-one timing basis. The time $T_{atr}$ is an arbitrarily determined time between the end of the atrial refractory period and the end of the escape interval. As discussed below, this time is used to define a window $T_{ar3}-T_{atr}$ which is used, in one embodiment of this invention, to determine whether a sensed atrial rate is physiological. In a first embodiment, if an atrial signal is sensed within the physiological $T_{ar3}-T_{atr}$ window, then the pacemaker enables the $T_{ar2}-T_{ar3}$ window for the next cycle. Last, the time $T_{aa}$ is the atrial escape interval, which also defines the pacer interval where there is a complete time out from one atrial stimulus or spontaneous P wave to the next.

Figure 3A:
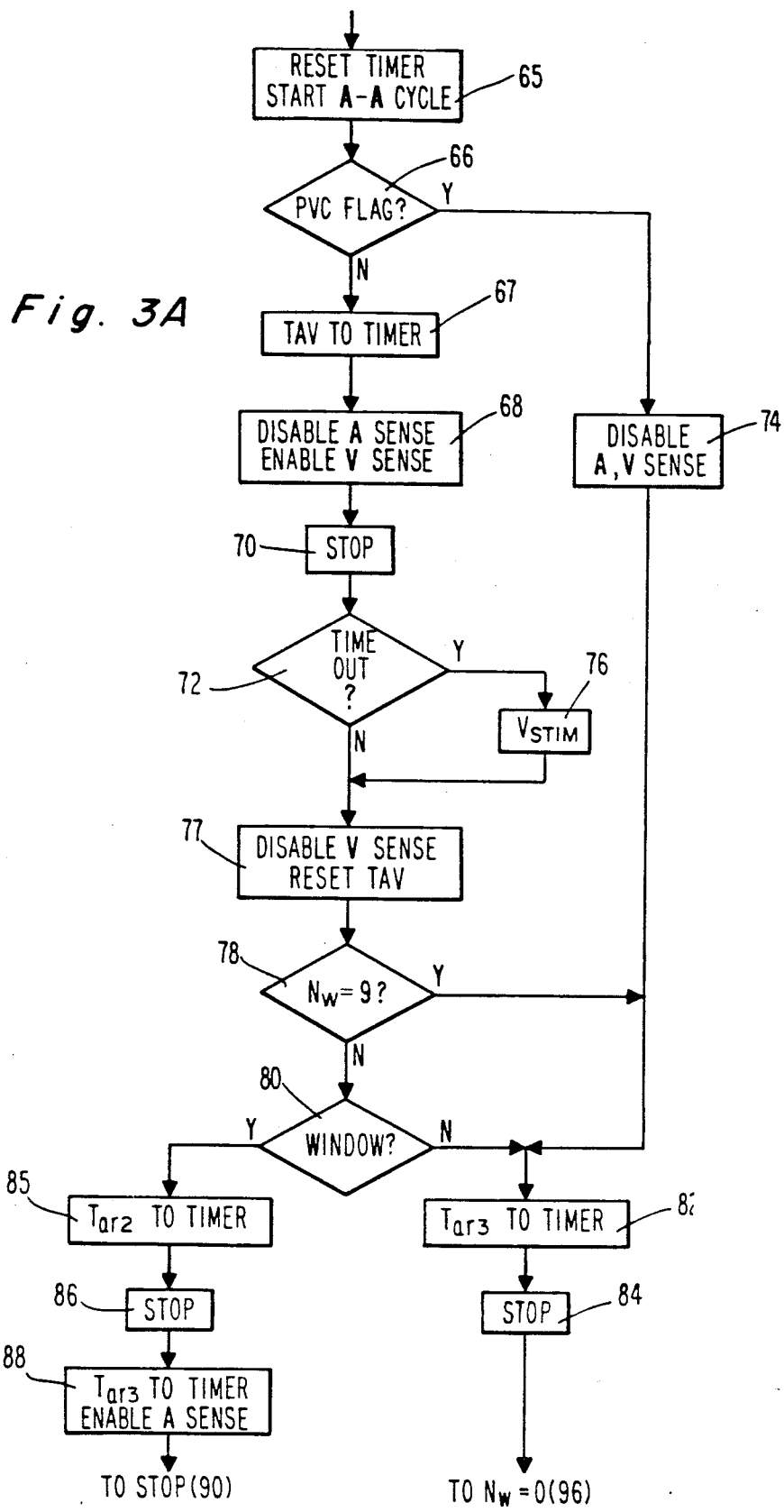
FIGS. 3A and 3B combined constitute a flow diagram showing the primary steps performed in the practice of the first embodiment of this invention, during each pacer cycle. While the steps are illustrated as a software flow diagram, they can be performed by any equivalent hardware embodiment.
Figure 3B:
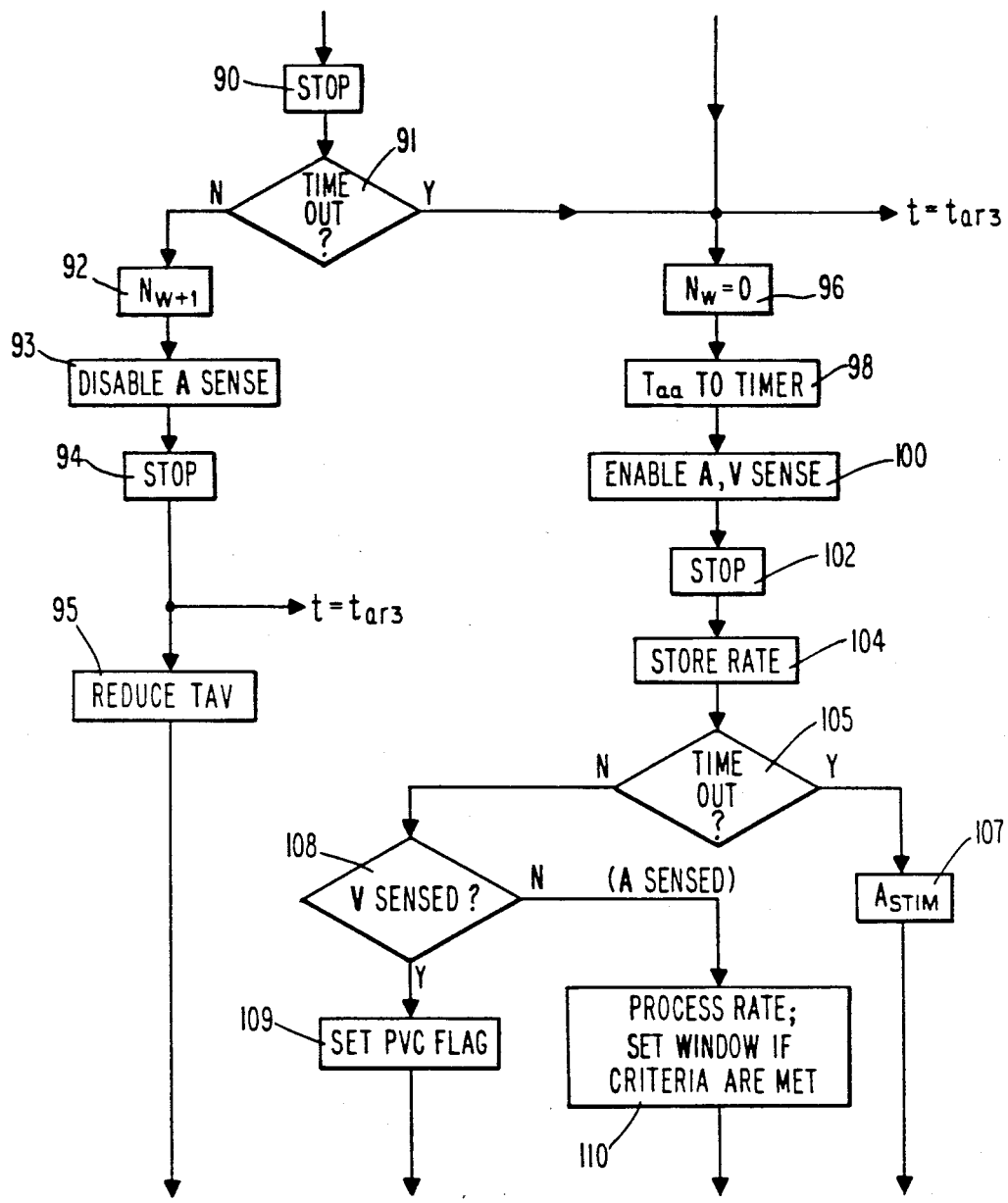

Referring now to FIGS. 3A and 3B, there is shown a flow diagram which represents the primary steps taken in the practice of this invention. This flow diagram is represented to illustrate steps taken under microprocessor control, i.e. this is a software flow diagram for the preferred embodiment. It is to be understood that this is a condensed flow diagram which illustrates only the steps necessary to set forth the preferred embodiment, and is not represented to be a complete flow diagram which illustrates all steps taken each cycle by the pacer. Clearly there are a lot of bookkeeping functions, well known in the art, and other operating functions which are performed each cycle, which steps need not be shown in order to illustrate the invention. Reference is made to co-pending applications Ser. Nos. 436,411, 436,457 and 436,454, incorporated herein by reference, for examples of other operations which may be carried out by the microprocessor controlled pacemaker.

Referring to the start of the flow diagram, at block 65 the pacer timer is reset, which represents the start of the A—A cycle. At block 66, it is determined whether the PVC flag has been set, i.e., whether there was a detected PVC last cycle. If yes, the A and V sense circuits are disabled at block 74, and the program branches to block 82. The PVC flag must be reset, and this can be done following block 66, or between blocks 98 and 100, for example. If no, it proceeds to block 67, where the stored value of $T_{AV}$ is sent to the timer, such that when the timer reaches a time $t=T_{AV}$ the microprocessor is re-started. Following this, at block 68 the A sense circuitry is disabled and the V sense circuitry is enabled, and the microprocessor stops (block 70) until the next event. At block 72, at which time the microprocessor has started to run again, it is determined whether the timer has in fact timed out to $T_{AV}$. If no, this means that a natural ventricular beat occurred and was sensed. If yes, the program branches to block 76, and causes the pacemaker to generate and deliver a ventricular stimulus. Following this, at block 77 the V sense circuitry is disabled, and $T_{AV}$ is reset to its normal value (in the event that it had a reduced value, as is discussed below). At block 78, a determination is made as to whether $N_W$, the number of consecutive P signals that have been sensed in the window W, if any, is equal to 9. If the answer is yes, meaning that 9 consecutive P wave signals have been sensed in the W window, this is an indication of stability of the V-A interval, caused by retrograde P waves, and thus a sign of a possible pacemaker induced or promoted tachycardia. In this event, the program branches to block 82. If $N_W$ does not equal 9, the pacemaker proceeds to block 80, and determines whether the window W is set. If the answer is no, the pacemaker proceeds to block 82, where $T_{ar3}$ is sent to the timer, and the microprocessor stops at block 84 to wait for a time out at $t=T_{ar3}$. If, at block 80, it is determined that the window W is set, at block 85 $T_{ar2}$ is sent to the timer, and the microprocessor stops at 86 to wait for time $T_{ar2}$, the start of the window W. When this time occurs, the microprocessor starts again, and at block 88 sends $T_{ar3}$ to the timer and, enables the A sense circuitry, following which it stops at block 90 to await either the sensing of a P wave signal or the time out of $T_{ar3}$.

As shown at block 91 (FIG. 3b), if it is determined that there is time out at $t=T_{ar3}$, the pacer branches to block 96 where $N_W$ is set to zero. However, if there was not a time out, indicating that a P signal was sensed within the window W, the program branches to block 92, where $N_W$ is incremented to $N_W+1$. The A sense circuitry is then disabled at block 93, and the microprocessor stops at block 94 to await the time out of t equal to $T_{ar3}$. At that time, which is the end of the window W, the pacer reduces the normal value of $T_{AV}$ at block 95, and recycles to block 65 where the timer is reset, to start a new cycle. The reduction in $T_{AV}$ is made because of the time delay between the natural occurrence of the P wave and the end of the window at $T_{ar3}$. If this time interval were not accounted for, the total A-V delay, or time between the atrial beat and the ventricular stimulus, would be longer than normal, a condition which the apparatus of this invention is designed to avoid. Although the reduction of $T_{AV}$ may be set arbitrarily by any factor stored in RAM or ROM, one suitable technique is to reduce $T_{AV}$ by one-half the window W, since the average delay from the sensed P wave to the end of the window is W/2. Thus, for a window length of about 100 ms, the reduction is 50 ms. Alternately, the pacer can employ a correlation between $T_{AV}$ and AA time, such as discussed below in connection with FIG. 4.

Returning to block 96, which is reached when there has been a time out at block 91, the time t is $T_{ar3}$, the end of the normal atrial refractory period. Accordingly, the atrial escape interval $T_{aa}$ is sent to the timer at block 98, and both the A and V sense circuitry are enabled at block 100, prior to stopping the microprocessor at 102. The microprocessor is started again either due to the time out, which means that an atrial stimulus is to be delivered, or due to a sensed signal, atrial or ventricular. The cycle rate is stored at block 104, and at block 105 it is determined whether there has indeed been a time out. If yes, an atrial stimulus is delivered, as shown at block 107. If no, it is determined whether a ventricular signal was sensed. If yes, the flow diagram branches to block 109, where the PVC flag is set because the sensed ventricular signal occurred without a prior sensed atrial signal, which is defined as a condition of a premature ventricular contraction. If the answer in block 108 is no, this means that an atrial signal has been sensed, and the computer proceeds to block 110 to process the rate which has been stored at block 104.

The functions carried out at block 110 are designed to make a determination as to whether the early atrial signal represents an increased physiological rate, and thus whether the window W should be established. Note that if the rate simply jumps from a normal rate at a value somewhere below the predetermined maximum directly to a rate that falls within the window W, the atrial signal is not sensed since the window W is not enabled. This is the usual condition where the signal falls within the refractory period. It is, of course, desirable not to act upon an earlier sensed atrial signal where, for example, that sensed signal actually represents noise of some sort or an atrial tachycardia. In the process and apparatus of this invention, the pacer processes the rate to see if there has been an increase toward the predetermined maximum rate, which increase can be considered to be of a natural, or physiological origin. This can be done in several different ways, in the practice of this invention.

In accordance with a first technique, at block 110 the pacemaker examines to see if the last beat fell within the $T_{ar3}$-$T_{atr}$ window, or predetermined range of time. If so, this indicates an atrial beat at a rate higher then normal, but still below the predetermined maximum, and such beat is deemed to be physiological, meeting the predetermined criterion for setting the window W. In this case, the W flag is set, such that during the next cycle the pacemaker branches on the Y path at block 80. The time $T_{atr}$, which represents the upper end of the physiological search window, can be set at any predetermined value as selected by the operator, and stored in memory. In another embodiment, the pacemaker may take the differential between the rate stored for the prior cycle and the most recent rate, or process the rate over a plurality of successive cycles, applying a predetermined algorithm to determine whether there has been an increase in rate which is deemed to be a physiological increase, whereby the criteria for setting the window are met. It is to be understood that the rate may thus be processed in any one of a number of different ways, the window being set or not set in accordance with whether the processed rate meets predetermined logical criteria. The embodiment of FIGS. 4 and 5 presents a preferred method.

The embodiment of FIGS. 3A and 3B presents, by way of a first example, an embodiment for determining the stability of the V-A interval. This is shown as being done by counting the number of P signals that occur within the window, and after the count reaches a predetermined number, altering the pacer operation so as to avoid a retrograde P wave, thereby breaking up the tachycardia. In the embodiment of FIGS. 3A and 3B, after the ninth consecutive P wave signal is sensed, a V stimulus is delivered at block 76, and then the pacer waits until the end of the normal refractory period at $t = T_{ar3}$ to enable sensing, i.e., it skips the window sensing. Under these conditions, if a tenth consecutive retrograde P wave occurred, it would not be sensed for timing purposes.

A preferred and more automatic embodiment of a DDD pacemaker system is illustrated by FIGS. 4A, 4B, 5 and 6A-C. With this embodiment, the pacemaker makes an automatic decision, based upon the patient history, as to what operative atrial refractory period is utilized. In other words, under certain circumstances, the pacemaker will go into the Wenckebach mode of operation, wherein the operative end of the atrial refractory period occurs at a first time ($T_{ar2}$). Under another set of circumstances, determined by the pacemaker, the pacemaker goes into a "block" mode of operation, whereby high atrial rates are treated by blocking every other or every two out of three sensed atrial signals from producing a ventricular stimulus, thereby producing an atrial rate/ventricular stimulus rate ratio of 2:1 or 3:1. The important point of this arrangement is that the shorter atrial refractory period associated with the Wenckebach mode is utilized only when the pacemaker has determined that the high atrial rate is "physiological", thereby protecting against the circumstances which, in other prior art systems, lead to pacemaker mediated tachycardia when the Wenckebach mode is used.

Figure 4A:
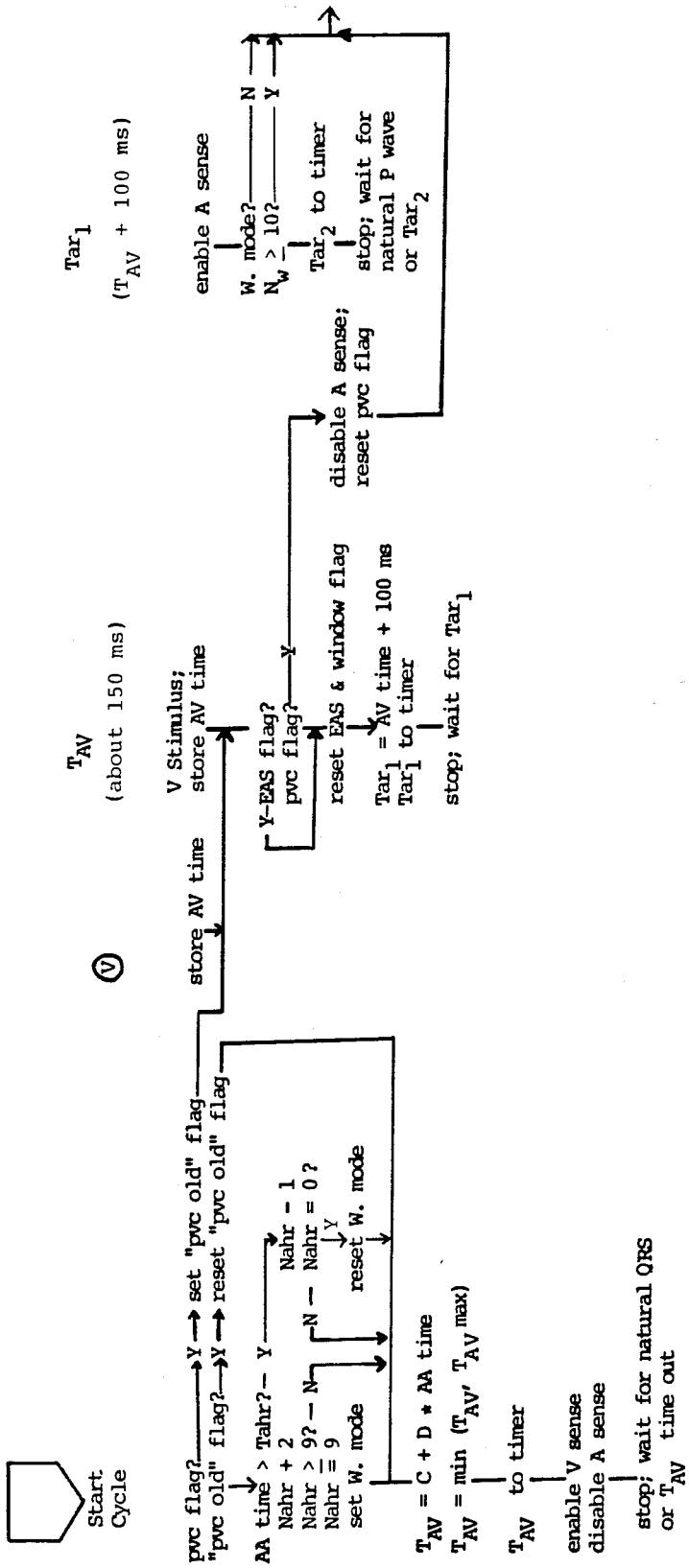
FIGS. 4A and 4B comprise a timing diagram of an improved embodiment of the dual chamber pacing system of this invention.
Figure 4B:
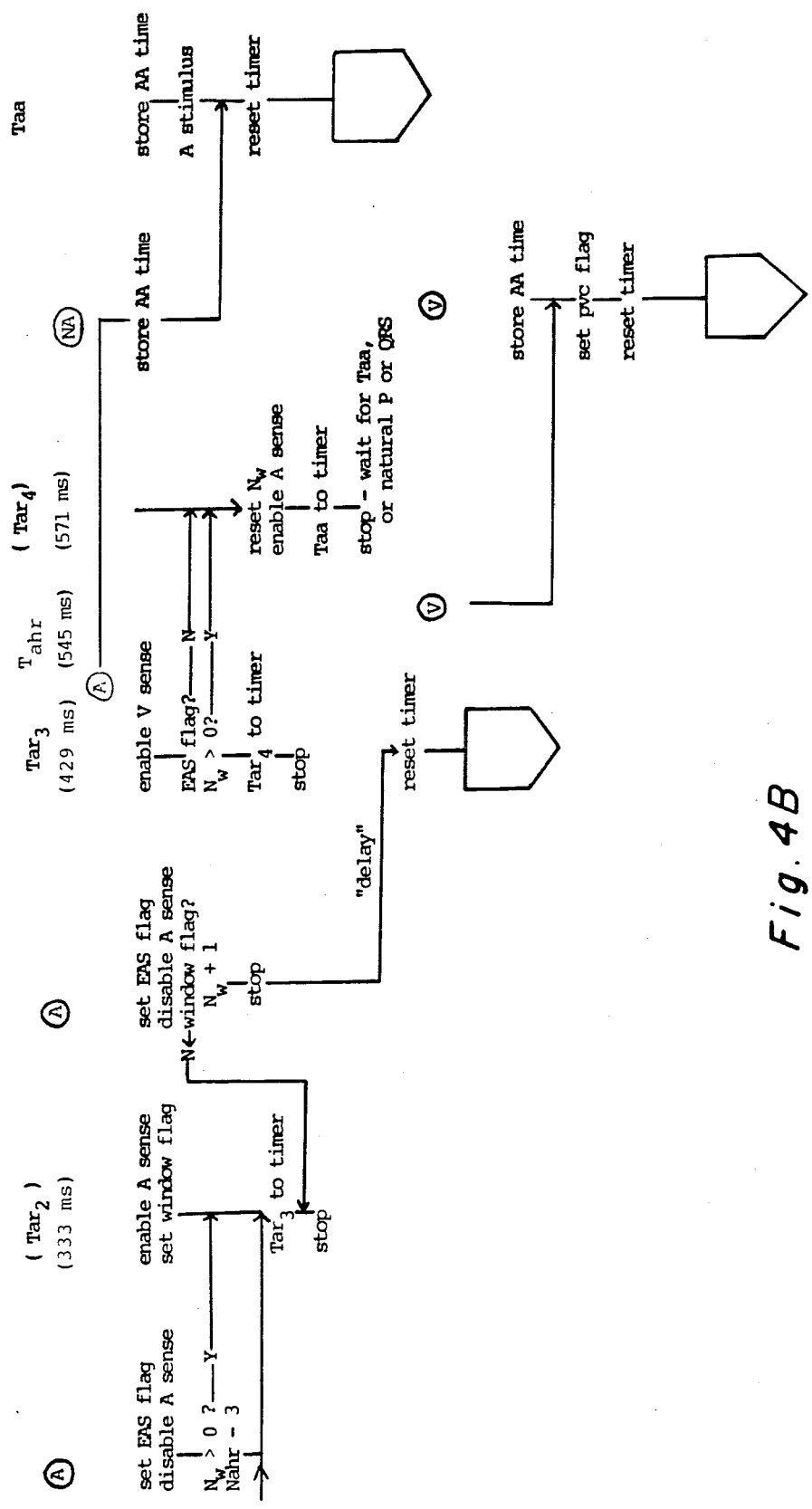

Referring to the timing diagrams of FIGS. 4A and 4B, there are indicated at the top a plurality of times. The times shown in parenthesis ($T_{ar2}$, $T_{ar4}$) may or may not be read into the timer during a given cycle; the other times, e.g. $T_{AV}$, $T_{ar1}$, $T_{ar3}$ and $T_{aa}$ are read into the timer each cycle. The start of the cycle is the atrial sense or atrial stimulus event. $T_{AV}$ is the time out of the AV delay, at which time a stimulus is delivered to the ventricle (in the event of no natural ventricular beat). $T_{ar1}$ (e.g., 250 ms) is the end of the absolute atrial refractory period, i.e. the time when the pacemaker starts looking to sense the presence of any atrial signal, whether or not it is going to act on the sense signal. $T_{ar2}$ is the beginning of the Wenckebach window, or the end of the operative refractory period when the pacer is in the Wenckebach mode. The Wenckebach window is between time $T_{ar2}$ and $T_{ar3}$, $T_{ar2}$ being typically 333 ms and $T_{ar3}$ being typically 429 ms. During Wenckebach mode operation, the pacer looks to see if a sensed P has occurred within that Wenckebach window. $T_{ar3}$ is the end of the Wenckebach window, and is also the end of the normal atrial refractory period, the time that sets the normal maximum rate. $T_{ahr}$ is a high rate time established to provide a measure of whether sensed high atrial rates are physiological, and in this example may be 545 ms. $T_{ar4}$, suitably 571 ms in this example, is the operative end of the atrial refractory period for the block mode. Also shown at the top of FIGS. 4A and 4B are the symbols V and A, which indicate that a V signal or A signal can be sensed at this time.

Starting at the beginning of FIG. 4A, which is the start of the pacer cycle, the pacer looks to see whether the PVC flag is set. If yes, meaning that there was a PVC in the just prior cycle, then the pacer sets the "PVC old" flag, skips generating the AV time and generating a V stimulus, and goes to the part of the program indicated under $T_{AV}$. Note that there, since the PVC flag is set, nothing is done, but the program disables the A sense, resets the PVC flag and carries on. Continuing back at the start, if the PVC flag has not been set in the just prior cycle, the program checks to see if the "PVC old" flag is set, meaning that cycle before last there had been a PVC. If yes, the "PVC old" flag is reset and the program branches to set $T_{AV}$. If no, the program determines whether the cycle time (AA time) was greater than the reference time $T_{ahr}$. $T_{ahr}$ is the comparison time for the "physiological" window that looks to see whether there are physiological high rates existing in the atrium, i.e., the pacer looks to see if there are five consecutive beats within the physiological window between $T_{ar3}$ and $T_{ahr}$, and if so then automatically goes into the Wenckebach mode. If the atrial cycle time is greater than $T_{ahr}$, meaning a lower rate, then the number of consecutive physiological stimuli ($N_{ahr}$) is reduced by one. The program looks to see whether $N_{ahr}$ is now equal to zero (it cannot be set to a negative number, but can only go down to zero, and) only if so the Wenckebach mode is reset.

If the atrial cycle time has been found to be less than $T_{ahr}$, then $N_{ahr}$ is incremented by adding 2. This has happened because the atrial beat occurred between $T_{ar3}$ and $T_{ahr}$. Note that the cycle time could not have been registered as occurring before $T_{ar3}$, because if so there would have been a "block" situation. If the pacer senses an early atrial sense (EAS), meaning a sensed atrial signal before $T_{ar2}$ or $T_{ar3}$, the pacer times out through $T_{ar3}$, and then puts $T_{ar4}$ into the timer, to give the "block" high rate limit. Since $T_{ar4}$ (571 ms) is set just a bit above $T_{ahr}$ (545 ms), the atrial cycle (AA) time—which was $T_{ar4}$—is greater than $T_{ahr}$, and in this situation the signal is not viewed as having been in the physiological sense window, i.e., the EAS is "non-physiological".

If $N_{ahr}$ has been counted to be equal to or greater than 9, such as would happen with five atrial signals in the physiological sense window ($T_{ar3}$ to $T_{ahr}$) without any decrementing, then the "Wenckebach" mode is set. The AV time out is calculated as a function of AA time according to the formula as shown, the pacer checks $T_{AV}$ for min and max, and $T_{AV}$ is sent to the timer. The V sense is enabled (to look for a natural V) and A sense is disabled. The pacer then waits for V sense, or time out of $T_{AV}$.

If a ventricular heartbeat spontaneously occurs before time out of $T_{AV}$, then this is noted and the AV time is recorded. If there is time out of $T_{AV}$, then a V stimulus is delivered and the AV time is recorded. In both events, at $T_{AV}$ the pacer checks to see if the early atrial sense (EAS) flag is set. If yes, it skips to reset the EAS flag and the Wenckebach window flag. Note that the window flag has to be reset every cycle, and this is a convenient place to do it. If there is no EAS flag, the program checks to see if there is a PVC flag. If no, the EAS and window flags are reset; $T_{ar1}$ is set to the AV time plus 100 ms; $T_{ar1}$ is sent to the timer and the microprocessor stops. Thus, when there is a sensed ventricular signal, the program undertakes the same steps as occur at $T_{AV}$ when there is a stimulus delivered.

If there has been a PVC flag, note that the program branches, disabling A sense and resetting the PVC flag. The program goes directly to set $T_{ar3}$ to timer, and waits for $T_{ar3}$ to time out. In this event there is no time out of $T_{ar1}$, and the steps indicated at $T_{ar1}$ are not taken. Otherwise, (i.e., for no PVC) when $T_{ar1}$ is timed out, the A sense is enabled and the program checks to see if it is in Wenckebach mode. If no, then the program carries on, and $T_{ar3}$ is put into the timer. If the answer is yes, then the question is, have there been 10 consecutive atrial signals within the Wenckebach window ($T_{ar2}$-$T_{ar3}$) If yes, meaning that a ventricular stimulus is to be skipped, $T_{ar2}$ is not put into the timer, but rather the program jumps forward and puts $T_{ar3}$ into the timer. Note then that if an atrial signal comes within the Wenckebach period, between $T_{ar2}$ and $T_{ar3}$, there is a delay and the timer is not reset until $T_{ar3}$ has been timed out. Still back at $T_{ar1}$, if $N_W$ is less than 10, then $T_{ar2}$ is put into the timer, so that the pacer looks for signals which occur within the Wenckebach window.

If an atrial signal is sensed following $T_{ar1}$ (the absolute refractory interval) and before $T_{ar2}$, the EAS flag is set and the A sense is disabled; the pacer then determines whether $N_W$ is greater than zero (which is the case when the pacer has been operating in the Wenckebach mode of operation in the preceding cycle or cycles.). If yes, the beat has shifted out of the window and the pacer does not increment $N_W$, but goes directly to put $T_{ar3}$ into the timer. If no, an abrupt rate increase in the atrium, then $N_{ahr}$ is decremented by a count of three, and $T_{ar3}$ is put into the timer.

If $T_{ar2}$ is timed out (meaning that the Wenckebach mode has been designated), then A sense is enabled and the window flag is set. Then $T_{ar3}$ is put into the timer and the pacer waits to see what happens between $T_{ar2}$ and $T_{ar3}$. If an atrial signal occurs within that window, the EAS flag is set and A sense is disabled; if the window flag had not been set (meaning no Wenckebach mode), then the pacer ignores this particular signal for the present, such that the choice is to go into block rather than go into Wenckebach. When $T_{ar3}$ is timed out, only if the pacer has detected an EAS and is not in the Wenckebach mode, then $T_{ar4}$ is put in the timer, meaning a 2:1 or 3:1 block with decreased upper rate limit ($T_{ar4}$).

When an atrial signal is sensed between $T_{ar2}$ and $T_{ar3}$, and the window flag is set, $N_W$ is incremented to $N_W+1$, and the microprocessor stops. When the timer times out to $T_{ar3}$, the end of the window, the timer is reset and the program returns to the start. This provides the "delay" between occurrence of a sensed atrial signal within the window and the timing out of $T_{AV}$.

When $T_{ar4}$ has not been put in the timer, $N_W$ is reset, since there have not been consecutive signals within the Wenckebach window. The A sense is enabled, and $T_{AA}$ is put into the timer so that an atrial signal can be sensed any time up to the end of the pacer interval. If a ventricular signal occurs between $T_{ar3}$ and $T_{ar4}$, or a ventricular signal is sensed after $T_{ar4}$ but before $T_{AA}$ or the occurrence of an atrial beat, this means a PVC has occurred, and pulsing the atrium should be avoided; accordingly, the PVC flag is set and the timer is reset (to 0). Thus, in the case of a PVC, there is no atrial pulse.

Last, if an atrial signal is sensed after $T_{ar3}$, the AA time is stored and the timer is reset. Likewise, if $T_{AA}$ times out, an A stimulus is delivered and the timer is reset. Note that for an atrial signal sensed between $T_{ar1}$ and $T_{ar2}$, the pacer never goes into the Wenckebach mode because A sense is disabled until $T_{ar3}$ or $T_{ar4}$, meaning it is in "block" mode.

Figure 5A:
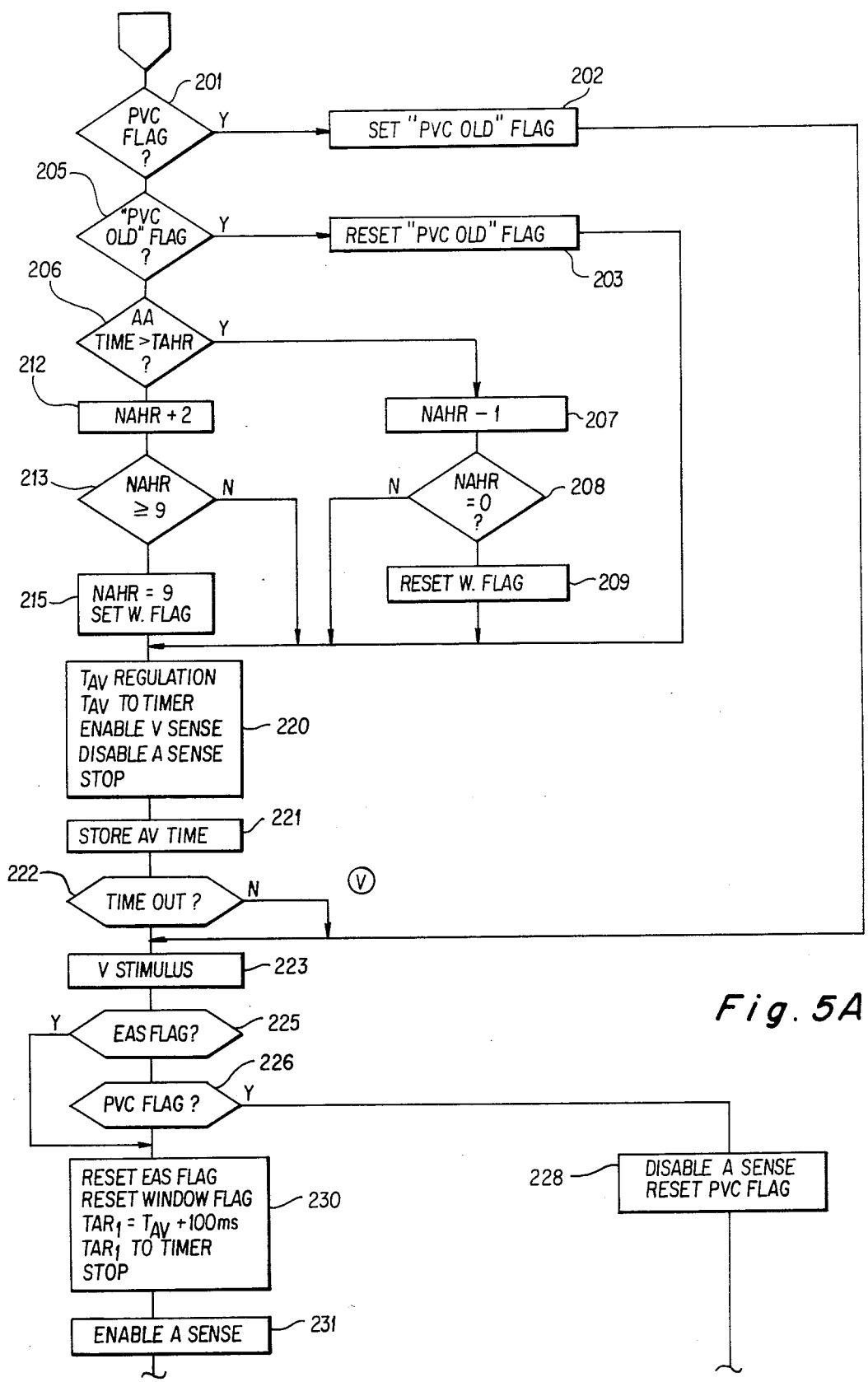
FIGS. 5A and 5B combined constitute a flow diagram of the software used in the embodiment illustrated in FIG. 4.
Figure 5B:
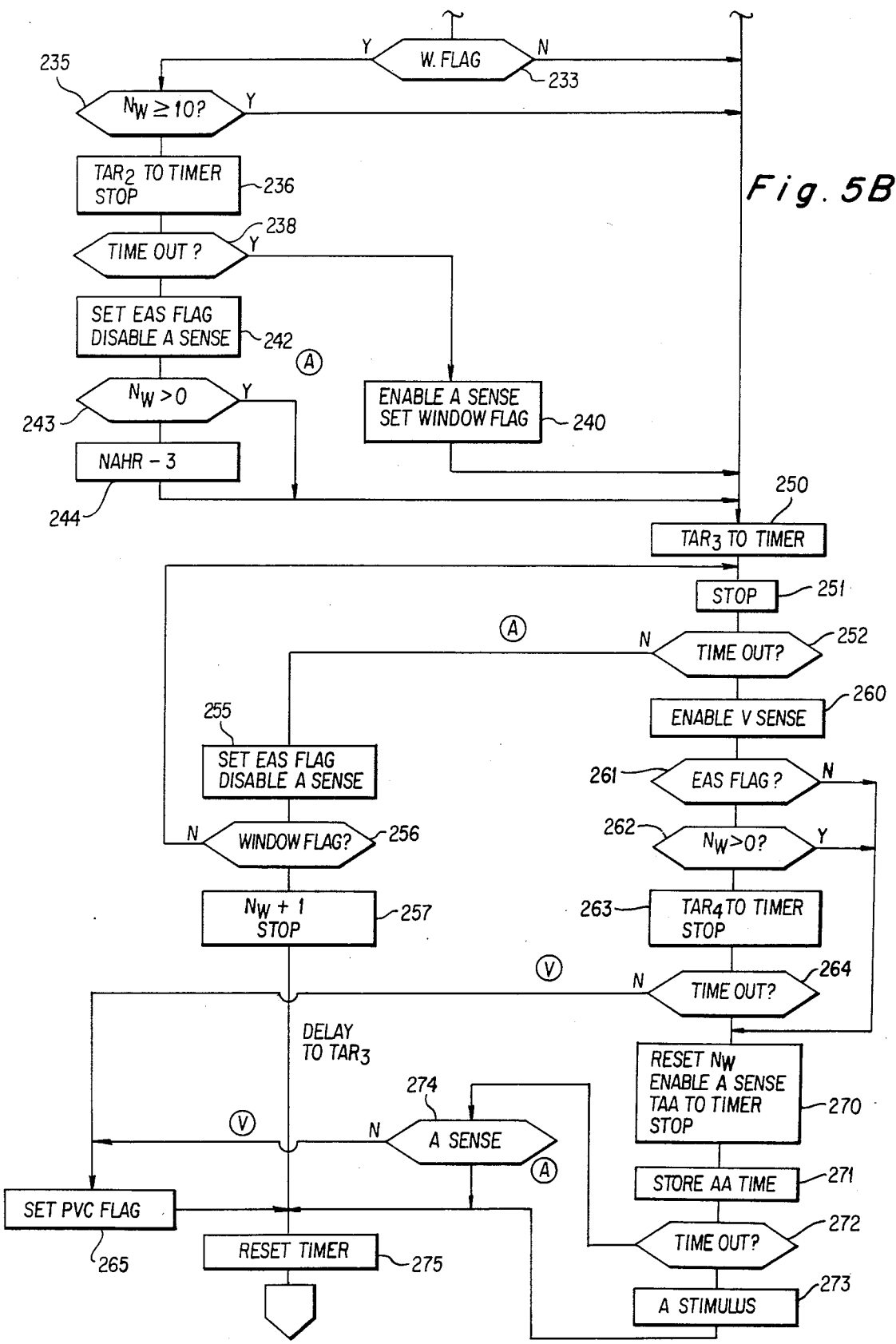

Referring now to the software flow diagram, FIGS. 5A and 5B the first set of instructions are the same as shown at the far left of the timing diagram. Thus, blocks 201-203, 205-209, and 212-215 show the same steps as set forth under "start cycle" of the timing diagram, and are carried out by the microprocessor in the manner illustrated. At block 220, $T_{AV}$ is determined by the formula; $T_{AV}$ is sent to the timer; V sense is enabled and A sense is disabled, and then the microprocessor stops. When the microprocessor starts up again, the AV time is stored at 221, and at 222 it is determined whether there has been a time out, or a sensed V. If it has been a sense, the program loops past block 223 which commands delivery of a V stimulus. Of course, if there has been a time out, then a V stimulus is delivered. Next, at 225 the program determines whether there has been an EAS. If yes, the program branches; if no, at 226 it determines whether the PVC flag is set. If yes, meaning that there was a PVC which terminated the end of the last pacer cycle, then at 228 A sense is disabled and the PVC flag is reset. The program then branches to block 250 to put $T_{ar3}$ into the timer (it isn't going to look for any atrial signals in the Wenckebach window). Assuming there had been no PVC flag, then at 230 the EAS flag is reset; the window flag (Wenckebach) is reset; and $T_{ar1}$ is computed and put into the timer. The microprocessor then stops. When it starts again, since it is not possible that there has been a sense signal, there is no determination as to whether there has been a time out. The A sense is enabled at 231; the program looks at 233 to see if the Wenckebach flag is set. If no, the program branches, and $T_{ar3}$ is put in the timer, following which the pacer waits to see what happens (i.e. is there a sense signal or does the timer time out at $T_{ar3}$?). If the Wenckebach flag is set, then the pacer must look for $T_{ar2}$, to define the Wenckebach window. It branches to block 235 and determines whether $N_W$ is equal to or greater than 10. If yes, a ventricular stimulus is to be skipped (pacer doesn't reset due to a sensed P in the window), so that the pacer branches to immediately put $T_{ar3}$ into the timer at block 250. If $N_W$ has not reached 10, then $T_{ar2}$ is put into the timer at 236 and the microprocessor stops. When it starts again, it is determined at 238 whether or not there has been receipt of an atrial signal before $T_{ar2}$. If there has been a time out, at 240 the A sense is enabled and the window flag is set, and at 250 $T_{ar3}$ is put into the timer. If there has not been a time out, meaning that an atrial signal was sensed before $T_{ar2}$, at 242 the EAS flag is set and A sense is disabled. If $N_W$ was greater than zero (at 243), then the pacer branches and immediately sets $T_{ar3}$ into the timer. If $N_W$ was not greater than zero, i.e. it was zero, this means that this was the first look in the window, and $N_{ahr}$ is decremented 3 at block 244, meaning that the pacer is again operating in the physiological window and will recommence looking to see whether it should go into Wenckebach mode.

After $T_{ar3}$ has been set into the timer at 250, when the microprocessor starts again at 252 it determines if there was a time out. If no, then an atrial signal has been received (within the Wenckebach range of time); at 255 EAS flag is set and A sense is disabled. If the window flag has been set (at 256), meaning that the pacer is in Wenckebach mode, then $N_W$ is incremented at 257, and the microprocessor stops. Since $T_{ar3}$ is in the timer, only when the timer times out to $T_{ar3}$ does the program then reset the timer to start a new cycle. If the window flag has not been set (at 256), meaning that an atrial pulse happened to come along at a rate within the Wenckebach window but without the pacer being in the Wenckebach mode, the program recycles and again looks for a time out of $T_{ar3}$. If there has been a time out at 252, V sense is enabled at 260. If at 261 it is determined that the EAS flag has not been set, the pacer branches to block 270 to reset $N_W$ (by definition there have not been consecutive signals within the Wenckebach window); A sense is enabled; and $T_{AA}$ is put into the timer. If there has been an EAS, and $N_W$ is determined at 262 to be not greater than zero (meaning we are not in Wenckebach), then $T_{ar4}$ is set into the timer, since the pacer is in a "block" mode of operation. If, at 264, a ventricular stimulus comes along before the end of $T_{ar4}$, this is interpreted as a PVC, and the PVC flag is set at 265 and the timer is reset at 275, starting a new cycle. Of course, likewise if after $T_{AA}$ has been set into the timer a ventricular signal is sensed (272,274), then the PVC flag is set. If an atrial signal is sensed at 274, then the timer is reset. If, at 272 it is determined that $T_{AA}$ has timed out, an A stimulus is delivered at 273, and then the timer is reset.

Figure 6A:
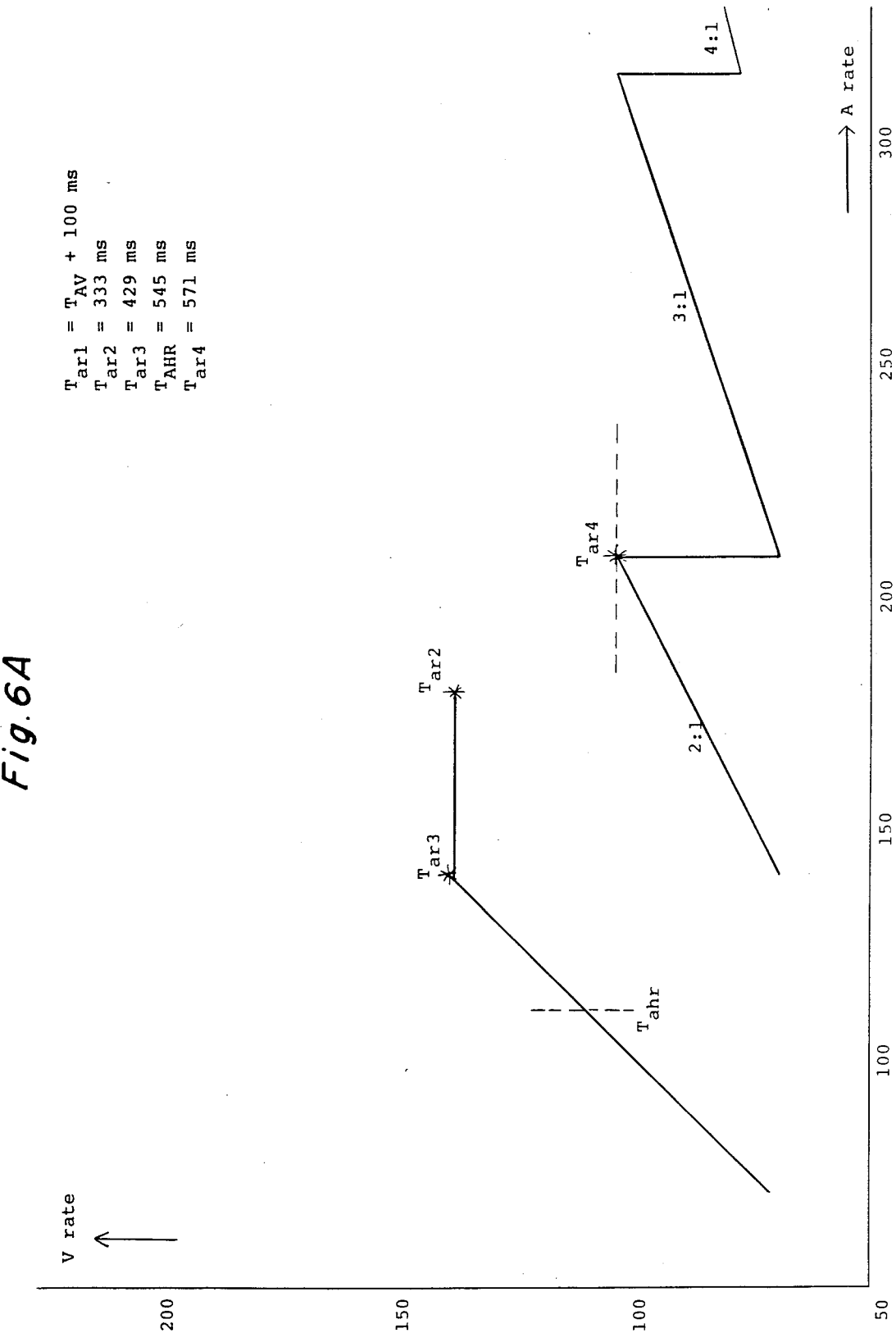
FIGS. 6A, 6B and 6C are rate diagrams illustrating the embodiment of FIGS. 4 and 5.
Figure 6B:
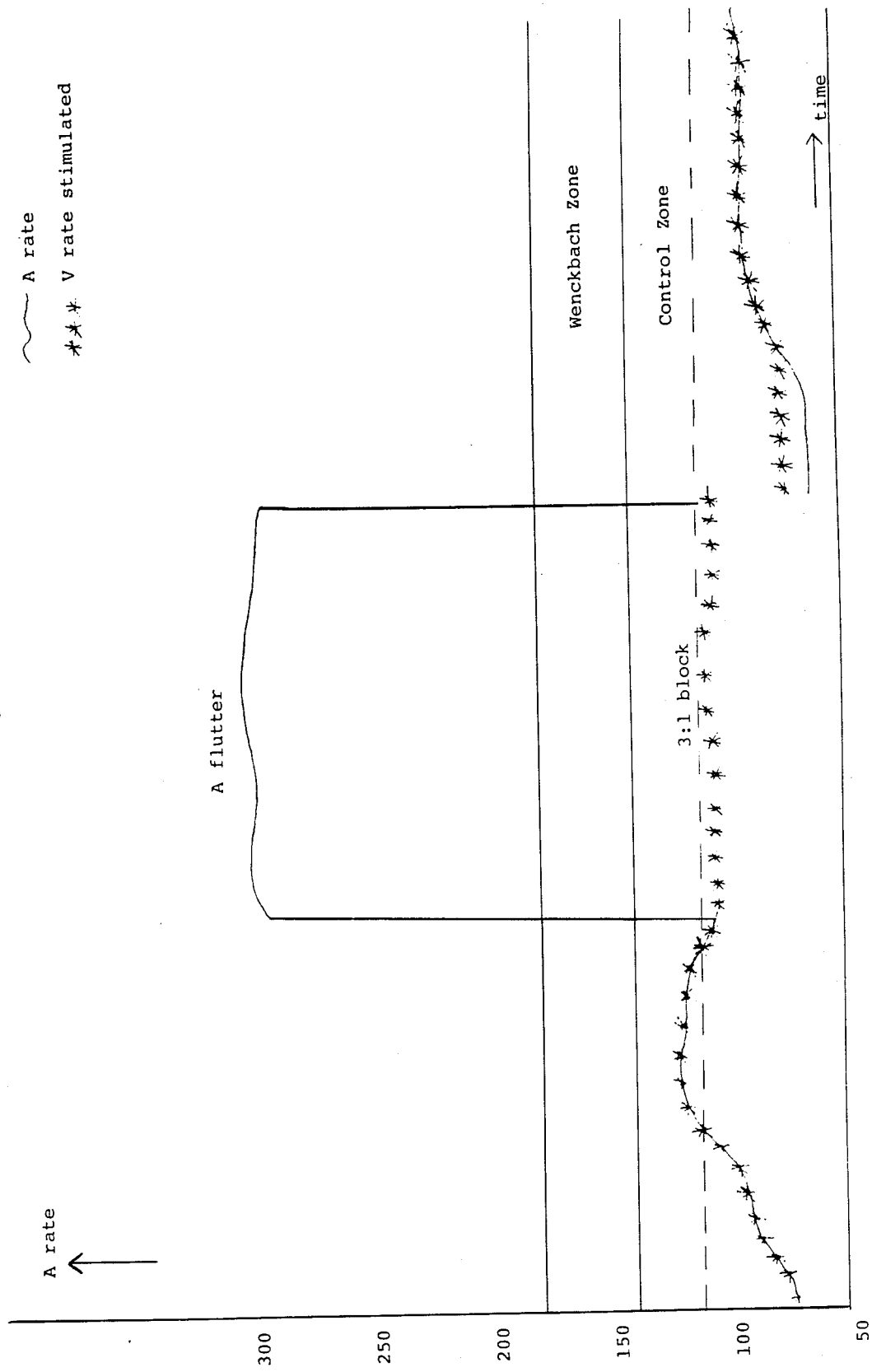
Figure 6C:
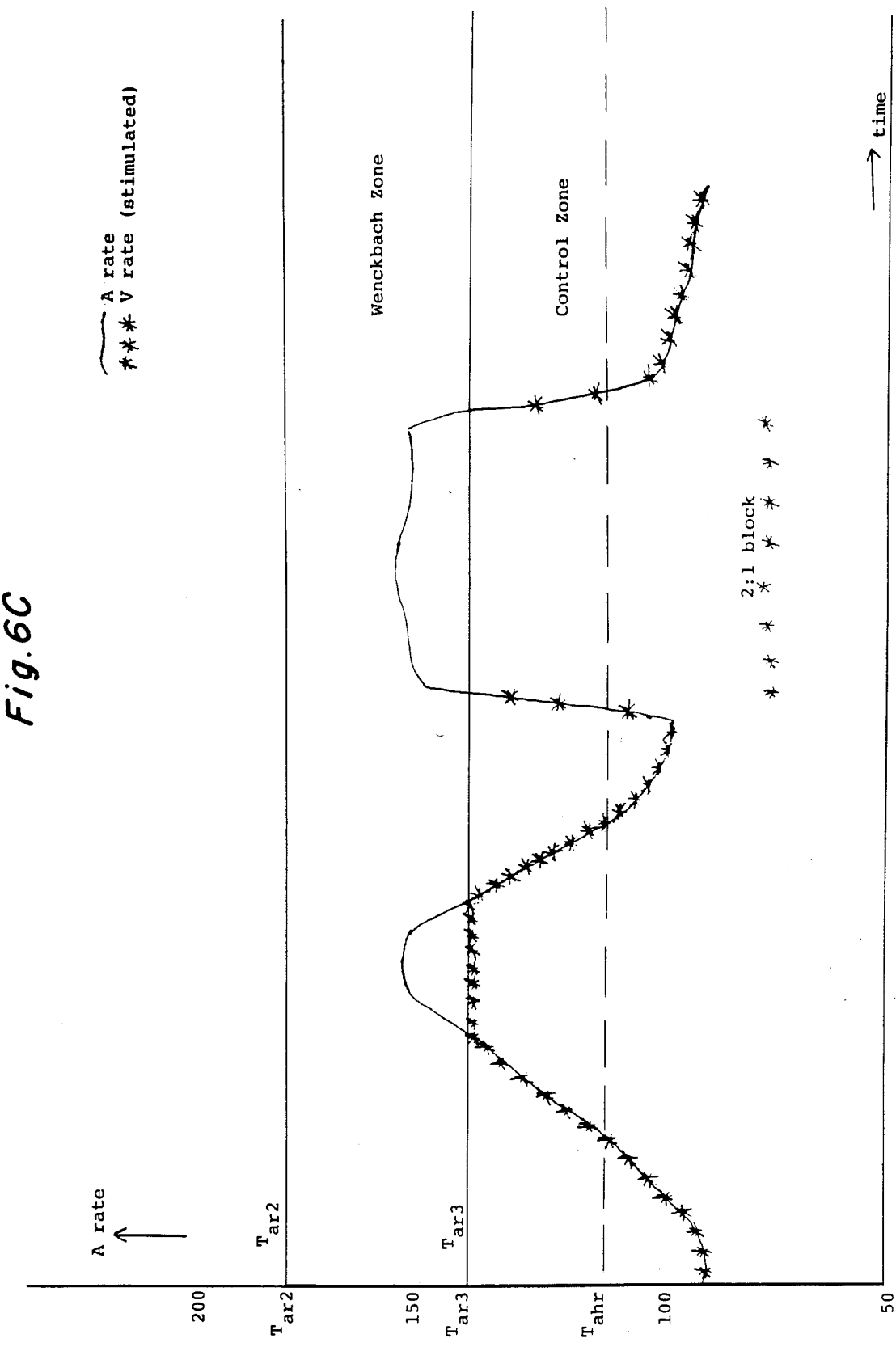

Referring now to FIG. 6A, there is shown a rate diagram which further illustrates the operation of the automatic embodiment. As illustrated, when in the Wenckebach mode, high atrial rate signals falling between $T_{ar2}$ and $T_{ar3}$ result in ventricular rates limited at a rate corresponding to $T_{ar3}$. However, in the block mode, there is a 2:1 ratio of atrial rate to ventricular rate up to a maximum atrial rate of twice that corresponding to $T_{ar4}$; and thereafter the ratio increases to 3:1 and 4:1, always with the same reduced maximum rate while in block mode. FIG. 6B illustrates the response of the pacer to high rate atrial flutter; FIG. 6C illustrates operation of the pacer in both the Wenckebach mode and in a mode of 2:1 block.

There is thus shown an embodiment of a dual chamber pacer with automatic selection of the mode of operation in the presence of high atrial rates, i.e., automatic selection of operative atrial refractory period. Thus, depending upon the recent monitored events, the pacemaker may operate at a normal refractory period (e.g., set by $T_{ar3}$); in the Wenckebach mode (with an atrial refractory period set by $T_{ar2}$); or in a block mode (with atrial refractory period set by $T_{ar4}$). For the preferred embodiment, the Wenckebach window is within the normal atrial refractory period (since it ends at $T_{ar3}$), and the block mode refractory period is longer than the normal one, since $T_{ar4}$ is greater than $T_{ar3}$. The advantages of the Wenckebach mode, where a delayed ventricular stimulus is delivered, are safely realized by automatically placing the pacer in this mode only when the recent patient history reveals that the sensed atrial signals are physiological. When sensed high atrial rates have not been determined to be physiological, in accordance with the programmed criteria, then the pacemaker system operates in a block mode, with a larger operative atrial refractory period which provides a lower maximum ventricular stimulus rate. As used herein, the sensed atrial signal is deemed to be physiological when conditions defined in an algorithm such as the one of FIG. 4A are met, i.e., $N_{ahr}$ is greater than 0. Although a particular preferred method of determining when high atrial rate beats are physiological has been disclosed, it is understood that other algorithms can be employed within the scope of this invention.

We claim:

1. A dual chamber pacemaker system having means for sensing atrial heartbeat signals and means for delivering ventricular stimulus signals in response to said sensed atrial signals, characterized by:

high rate means for detecting when sensed atrial signals have a high rate greater than a predetermined normal maximum rate;

delay means selectively operative when a said high rate is detected for delaying said ventricular stimulus signals relative to the preceeding sensed atrial signals so that the rate of said ventricular signals does not exceed said normal maximum rate;

block means selectively operative when a said high rate is detected for providing n:1 block rate selection means for automatically selecting when said delay means or said block means is operative, said selection means including means for detecting atrial heartbeat signals occurring at rates corresponding to a predetermined examination rate range below said normal maximum rate and logic means for selecting said delay means as a predetermined function of said heartbeat signals detected within said examination rate range.

2. The pacemaker system as described in claim 1, wherein said block means comprises means for limiting the maximum ventricular stimulus rate during block rate control to a rate lower than said normal maximum rate.

3. The pacemaker system as described in claim 1, wherein said delay means has means for detecting the occurrence of sensed atrial signals within a predetermined Wenckenback rate range above said normal maximum rate and means for controlling said delaying only in response to a detected said occurrence within said Wenckenbach rate range.

4. The pacemaker system as described in claim 1, wherein said logic means comprises counting means for counting a measure of the detected atrial heartbeat signals that occur within said examination rate range.

5. The pacemaker system as described in claim 1, wherein said logic means comprises means for accumulating data about the history of detected atrial heartbeat signals that occur within said examination rate range.

6. A dual chamber pacemaker system having means for sensing atrial heartbeat signals and ventricular stimulus means for delivering ventricular stimulus signals in response to said sensed atrial signals, characterized by:
   high rate analysis means for analyzing the timing of sensed high rate atrial signals having rates within a predetermined examination range of rates over a plurality of pacemaker cycles; and
   ventricular response control means for automatically controlling pacemaker response to atrial signals having rates within a predetermined range above a predetermined high rate in a Wenckebach mode of operation as a function of said analyzing.

7. A pacemaker system as described in claim 6, comprising AV delay means for timing out an AV delay between a sensed atrial signal and a responsive ventricular stimulus, and wherein said AV delay is a function of the just prior atrial cycle time.

8. The pacemaker system as described in claim 6, comprising means for normally delivering an atrial stimulus following a predetermined atrial cycle time, PVC means for detecting PVCs, and means for omitting delivery of an atrial stimulus following detection of a PVC.

9. The dual chamber pacemaker system as described in claim 6, wherein said high rate analysis means has means for setting the upper limit of said examination window at a rate of about said predetermined high rate.

10. The dual chamber pacemaker system as described in claim 6, wherein said high rate analysis means comprises means for determining a measure of the number of atrial signals having rates within said examination range over a consecutive plurality of pacemaker cycles.

11. The dual chamber pacemaker system as described in claim 6, further comprising block mode means for operating said ventricular stimulus means in a block mode of operation, and said ventricular response control means comprising means for choosing one of said Wenckebach or block mode of ventricular rate response as a function of said analyzing.

* * * * *